United States Patent [19]

Marquez

[11] 4,094,972

[45] June 13, 1978

[54] PROSTAGLANDIN USE IN PROLONGING AND INTENSIFYING FERTILITY IN POULTRY

[75] Inventor: Bernard James Marquez, East Lansing, Mich.

[73] Assignee: The Board of Trustees, Michigan State University, East Lansing, Mich.

[21] Appl. No.: 821,672

[22] Filed: Aug. 4, 1977

[51] Int. Cl.$^2$ .................. A61K 35/52; A61K 31/215; A61K 31/19
[52] U.S. Cl. ..................................... 424/105; 424/305; 424/317
[58] Field of Search ..................... 424/305, 317, 105

[56] References Cited
PUBLICATIONS

Verma et al., Chem. Abst. vol. 85, (1976), p. 104,358u.

*Primary Examiner*—Sam Rosen
*Attorney, Agent, or Firm*—Robert A. Armitage

[57] ABSTRACT

The present invention provides an improved method for artificial insemination of egg-laying hens (chickens and turkeys) whereby a poultry fertility-enhancing prostaglandin (POFEN-PG) is administered concommitantly with the insemination. Another aspect of the present invention provides for the insemination of hens with a semen-diluent mixture in which said POFEN-PG is contained in said diluent. Finally, there are disclosed compositions comprising the semen-diluent mixture containing the POFEN-PG and novel diluents containing POFEN-PG's.

19 Claims, No Drawings

PROSTAGLANDIN USE IN PROLONGING AND INTENSIFYING FERTILITY IN POULTRY

BACKGROUND OF THE INVENTION

The present invention provides an improved method whereby artificial insemination of turkeys and chickens is accomplished by administering concomitantly with said insemination a poultry fertility-enhancing prostaglandin (POFEN-PG).

A further aspect of the present invention is an improved method for the artificial insemination of hens whereby a semen-diluent mixture is employed in the insemination, said diluent containing a POFEN-PG.

Finally, the present invention particularly provides novel compositions of POFEN-PG's contained in poultry semen diluents and mixtures of said diluents containing a POFEN-PG with poultry semen.

The artificial insemination of poultry (e.g. turkeys and chickens) has obvious economic advantages as compared to reliance on natural insemination. In particular, the actual insemination of all egg-laying hens can be controlled and not left to the vagaries inherent in the natural process. More importantly the entire breeding stock of hens can be maintained in laying cages, rather than needing to roam about while awaiting a natural insemination. However, in view of the costs and difficulties in using artificial insemination as a method of producing fertile eggs, it has not heretofore been economically feasible in the case of chickens, and remains a costly exercise when employed commercially in turkeys.

In particular, artificial insemination in poultry requires that egg-laying capacity, fertility, and hatchability all be maintained at the high level observed in the case of successful natural insemination, and particularly be effective at maintaining fertility and hatchability for prolonged periods of time so as to reduce the number of inseminations required during the breeding season.

Accordingly, a method of artificial insemination in poultry which would not effect egg-laying capacity, while maintaining the intensity of the hens' fertility (the percentage of fertile eggs compared to total egg production), and prolonging the interval required between inseminations wherein intense fertility is observed, would increase cost efficiency of the operation. Moreover, any extended intervals between inseminations would cause a reduction in egg production losses invariably experienced each time a bird is handled and, equally importantly, reduce the number of males needed for insemination.

In order to maintain intense fertility in chicken hens, artificial insemination may be required once or twice per week during the egg laying season. See, for example, McCartney, M. G., Journal of Poultry Science 55:669-671 (1976), which described obtaining optimal fertility through artificial insemination by twice weekly inseminations with 0.05 mls. of neat semen. Further, see VanKrey, H. P., et al., Journal of Poultry Science 55:725-728 (1976) comparing insemination at nine or ten day intervals. This latter reference described the need to increase the number of spermatozoa inseminated in order to insure optimal fertility during the ten-day insemination interval. For earlier work on chicken insemination, see the semen volume and insemination schedules of Quinn, J. P. et al., J. Hered. 28:31-37 (1936), and Burrows, W. H., et al., Poultry Science 17:131-6 (1936).

As for the effect of prostaglandins on the female reproductive tract in poultry, see Day, S. A., The Role(s) of Prostaglandins in the Reproductive Physiology of the Hen, Dissertation Abstracts International 37(5):2106 (1976) which concludes that the effects of endogenous prostaglandins on the reproductive system seem to be exerted on the shell gland, a smooth muscle tissue, as opposed to those portions of the oviduct and related tissues where ovulation, fertilization, or sperm storage (i.e., the host glands) takes place.

SUMMARY OF THE INVENTION

In accordance with the present invention there are produced the following compositions:

(1) a mixture comprising
 (a) neat poultry semen and
 (b) a conventional poultry semen diluent containing an amount of a poultry-fertility enhancing prostaglandin (POFEN-PG) effective to intensify or prolong fertility in an egg-laying hen into which said mixture is inseminated per volume of said mixture to be inseminated into said hen, said semen and diluent being combined in a ratio sufficiently large to ensure an adequate number of spermatozoa per volume of mixture for fertilization and sufficiently small to ensure easy and complete intermixing of semen and diluent; and (2) a conventional poultry semen diluent, containing an amount of a POFEN-PG per volume of said diluent; which, when combined with neat poultry semen in a ratio sufficiently large to ensure an adequate number of spermatozoa per volume of mixture for fertilization and sufficiently small to ensure easy and complete intermixing of semen and diluent, results in a semen-diluent mixture containing an amount per volume of said mixture of said POFEN-PG effective to prolong or intensify fertility in an egg-laying hen following insemination of said hen with said mixture.

Moreover there are provided in accordance with the present invention improvements in the method for the artificial insemination of an egg-laying hen, wherein the improvements comprise:

(1) combining, in a ratio sufficiently large to ensure an adequate number of spermatozoa per volume of mixture for fertilization and sufficiently small to ensure easy and complete intermixing of semen and diluent, neat poultry semen with a conventional poultry semen diluent containing an amount of a POFEN-PG effective to prolong or intensify fertility in said hen when inseminated with the resulting semen-diluent mixture; or (2) concomitantly administering to said hen an amount of POFEN-PG effective to prolong or intensify fertility.

The present invention contemplates artificial insemination of egg-laying hens, specifically breeder hens. Accordingly, the economic utility of such breeder hens is in the production of live progeny, thus requiring that they produce high numbers of eggs which are both fertile and hatchable. Specifically, chicken and turkey hens are the objects of the present invention.

The present invention further comprises the use of poultry fertility enhancing prostaglandins, herein referred to as POFEN-PG's. These POFEN-PG's particularly include the natural prostaglandins of the PGA, PGE, and PGF series. Particularly, $PGA_1$ and $PGA_2$ are especially useful prostaglandins for the present purposes. Also useful are, however, the PGE compounds, i.e., $PGE_1$, $PGE_2$ and $PGE_3$, as well as PGF compounds of both the alpha and beta series, i.e., $PGF_1\alpha$, $PGF_2\alpha$, $PGF_3\alpha$, $PGF_1\beta$, $PGF_2\beta$ and $PGF_3\beta$.

In addition to the use of the natural prostaglandins as POFEN-PG's, certain analogs of these natural prostaglandins are likewise useful as POFEN-PG's. In particular, those analogs of prostaglandins which are capable of stimulating (i.e. contracting or relaxing) the smooth muscle tissues of the chicken or turkey oviduct are further useful as POFEN-PG's. More specifically, those prostaglandin analogs which are approximately equipotent to $PGA_1$ in this regard are especially preferred among prostaglandin analogs employed in the present invention.

As a readily available and convenient technique for measuring the ability of prostaglandin analogs to stimulate the avian oviduct, certain standard laboratory tests on mammalian smooth muscles are employed for convenience in determining those prostaglandin analogs which are useful herein as POFEN-PG's. In accordance with this simplified procedure for the identification of POFEN-PG's, see the gerbil colon smooth muscle stimulation test described by Weeks, et al., Journal of Applied Physiology 25:783-785 (1968). Accordingly, prostaglandin analogs which are equally potent to or more potent than $PGA_1$ in this assay are employed by the present invention as POFEN-PG's. In particular, such POFEN-PG's include 15-methyl-$PGA_1$, 15-methyl-$PGE_1$, 15-methyl-$PGF_2\alpha$, 16,16-dimethyl-$PGA_1$, 16,16-dimethyl-$PGE_1$, 16,16-dimethyl-$PGF_2\alpha$, 16-phenoxy-17,18,19,20-tetranor-$PGF_2\alpha$, 16-phenoxy-17,18,19,20-tetranor-$PGA_2$, as well as the ester, amide and salts of the prostaglandins (e.g., $PGA_1$, methyl ester) and other prostaglandin analogs known in the art.

The present invention particularly provides two improved methods whereby the instant POFEN-PG's are employed in artificial insemination. By a first embodiment of the present invention, the POFEN-PG is administered concomitantly with the insemination. While the administration of the POFEN-PG may be up to several hours before or several hours after insemination, most conveniently and economically the insemination takes place at or about the time the POFEN-PG is administered. Any systemic route of administration is employed but, for certainty and convenience in assuring that adequate levels of POFEN-PG are delivered at the appropriate time, intramuscular injection IM is the preferred systemic route for concomitant administration, although intravaginal (IV) administration may also be employed.

By another embodiment of the present invention, the POFEN-PG is administered intravaginally by mixture of the POFEN-PG with semen (IVAI). Accordingly, the POFEN-PG is first prepared in a pharmacologically acceptable form by combination with a conventional semen diluent and thereafter the diluent containing the POFEN-PG is mixed with the semen.

For the purpose of the present invention, the conventional poultry semen diluents include such recognized diluents as the Lake's diluent or the Beltsville extender. A wide variety of aqueous semen diluents, containing principally sodium glutamate with or without other salts for buffering, are known in the art or are prepared by methods readily available in the art. Accordingly, the conventional poultry semen diluents of whatever variety or whatever composition are all employed in the present invention.

Accordingly, the POFEN-PG, either as an oil or a solid, is dissolved in said aqueous diluent. Where necessary, the POFEN-PG may first be dissolved in a small amount of suitable solvent and thereafter be combined with said diluent to assure solubility of the POFEN-PG.

The amount of POFEN-PG to be dissolved in said diluent depends upon the ratio of semen to diluent in the semen-diluent mixture to be inseminated. Accordingly, the lower ratio of semen to diluent, the less POFEN-PG required per volume of diluent. However, for the purposes of the present invention any reasonable ratio of semen and diluent is employed. Thus, for example, when minimal dilution is desired, the semen to diluent ratio may be as large as is desired, provided that the viscosity of the semen is not so great as to prevent complete intermixing of the POFEN-PG-containing diluent with the semen. On the other hand, for example, maximal dilution (e.g., a small semen to diluent ratio) may be employed so long as sperm concentration in the resulting mixture is not so small as to interfere with fertilization. In particular, if said semen-diluent mixture is too semen-dilute, insufficient spermatozoa may be retained in the reproductive tract of the hen to permit the operation of the present invention.

Finally, the present invention describes a method which comprises the use of an "effective amount" of the POFEN-PG in the enhancement of fertility in the egg-laying hen. In accordance with the present invention, the administration of the POFEN-PG causes a dose related response in the reproductive tract of the egg-laying hen. Accordingly, at subthreshold doses no effect on fertility is observed, while in the dosage range contemplated for the present invention both intensification and prolongation of fertility is achieved. Finally, at higher doses, the hen exhibits undesired systemic effects from the POFEN-PG administration, including potentially a diminution of egg production and a reduction in the intensity and duration of fertility following artificial insemination. Accordingly, for each particular breed or strain of chicken or turkey, care must be taken to correctly determine and employ the proper dosage range contemplated by the present invention in order to assure that excessive amounts of POFEN-PG are not present and do not cause undesired side effects.

Accordingly, for POFEN-PG's such as $PGA_1$, dosages up to but not in excess of about 0.1-1.0 microgram per bird (IM) are employed. Moreover, dosages up to and including about one-tenth of the IM dose specified above are likewise employed in the present invention for intravaginal (IV or IVAI) dosing. For other POFEN-PG's, the appropriate dosage is determined by reference to the relative smooth muscle stimulatory potency of such other POFEN-PG's as compared to that of $PGA_1$. As indicated above, the preferred method for establishing such relative potency is employing the readily available and convenient gerbil colon smooth muscle assay described by Weeks et al. Thus, for example, when $PGE_1$ or $PGE_2$ is employed as the POFEN-PG, doses of about 1 to 10 percent of the dose of $PGA_1$ is sufficient.

Since, as indicated above, dosages will vary depending upon the sensitivity of the particular strain or breed of bird to the drug, the dosages specified herein may be adjusted upward or downward to obtain maximum prolongation and intensification of fertility. For example, dosages are first selected in the middle or lower range of values discussed above and thereafter successively increased while the intensity and duration of fertility is closely monitored. Dosages are thereafter adjusted upward until optimumization is achieved or systemic side effects prevent further elevation of dose.

Finally, in addition to the present novel methods disclosed herein, the invention further encompasses the diluents described herein containing the POFEN-PG's as well as the semen-diluent mixtures which contain such POFEN-PG's and are inseminated into egg-laying hens in accordance with the present methods.

DESCRIPTION OF THE PREFERRED EMBODIMENTS

The present invention is more thoroughly understood by the operation of the following examples describing the prolongation of fertility in chickens following administration with the POFEN-PG's.

EXAMPLE 1

PGA$_1$ in the Lake's diluent

Prostaglandin A$_1$ (2.0 micrograms) is mixed with Lake's diluent (Lake, P. E., Proceedings of the Fourteenth World's Poultry Congress, Madrid, Spain, 2:279-282, 1972) to a volume of 10 ml., yielding a concentration of PGA$_1$ of 0.2 µg./ml.

EXAMPLE 2

Semen-Diluent Mixture Containing PGA$_1$

The mixture of Example 1 (10 ml.) is combined with 10 ml. of neat chicken semen, yielding a semen diluent mixture containing PGA$_1$ at a concentration of 0.1 µg./ml. of mixture.

EXAMPLE 3

Insemination of an Egg-laying Hen with a Semen-Diluent mixture containing PGA$_1$ An egg-laying breeder chicken hen (a single comb white-leghorn, about 1 kg.) is artifically inseminated with 0.1 ml. of the semi-diluent mixture containing PGA$_1$ as described in Example 2. The insemination is thereafter repeated with the product of Example 2 at 14 day intervals during the egg-laying cycle of the hen, thereby maintaining a high level of fertility for a prolonged period between inseminations.

Further following the procedure of the Examples described above, there are prepared POFEN-PG-containing diluents and semi-diluent mixtures containing PGA$_2$, PGE$_1$, PGE$_2$, PGF$_2\alpha$, and PGF$_1\alpha$.

EXAMPLE 4

Insemination of an Egg-laying Hen Treated IM with PGA$_1$

Prostaglandin A$_1$ formulated for parenteral administration is injected intramuscularly (IM) into the breast muscle of an egg-laying breeder chicken hen (single comb white leghorn, about 1 kg.) in the amount of 0.1 µg. Immediately thereafter the hen is inseminated with 0.05 ml. of neat chicken semen. For the duration of the egg laying cycle of the hen, intramuscular injection of prostaglandin A$_1$ followed immediately by artificial insemination is repeated every 14 days. During the entire egg-laying cycle there is observed high fertility for a prolonged period between inseminations.

Following the procedure of Example 4 there is employed PGE$_1$, PGE$_2$, PGF$_1\alpha$, PGF$_2\alpha$, or PGA$_2$ in place of PGA$_1$.

I claim:

1. A mixture comprising
   (1) neat poultry semen and
   (2) a conventional poultry semen diluent containing per volume of said mixture to be inseminated into a hen, an amount of a poultry-fertility enhancing prostaglandin (POFEN-PG) effective to intensify or prolong fertility in an egg-laying hen into which said mixture is inseminated, said semen and diluent being combined in a ratio sufficiently large to ensure an adequate number of spermatozoa per volume of mixture of fertilization and sufficiently small to ensure easy and complete intermixing of semen and diluent.

2. A mixture according to claim 1 wherein said ratio is not more than 5:1 or less than 1:5.

3. A mixture according to claim 2 wherein said ratio is 1:1.

4. A mixture according to claim 3 wherein said POFEN-PG is PGE, PGE$_2$, PGF$_1\alpha$, PGF$_2\alpha$, PGA, or PGA$_2$.

5. A mixture according to claim 3 wherein said POFEN-PG is PGA$_1$.

6. A conventional poultry semen diluent, containing per volume of said diluent an amount of a poultry fertility-enhancing prostaglandin (POFEN-PG); which, when combined with neat poultry semen in a ratio sufficiently large to ensure an adequate number of spermatozoa per volume of mixture for fertilization and sufficiently small to ensure easy and complete intermixing of semen and diluent, results in a semen-diluent mixture containing per volume of said mixture an amount of said POFEN-PG effective to prolong or intensify fertility in an egg-laying hen inseminated with said mixture.

7. A diluent according to claim 6 prepared for combining in not more than a 5:1 ratio or less than 1:5 ratio of neat poultry semen.

8. A diluent according to claim 7 prepared for combining with neat poultry semen in a 1:1 ratio.

9. A diluent according to claim 8 containing PGE$_1$, PGE$_2$, PGF$_1\alpha$, PGF$_2\alpha$, PGA$_1$, or PGA$_2$ as said POFEN-PG.

10. A diluent according to claim 9 containing PGA$_1$ as said POFEN-PG.

11. In a method for the artificial insemination of an egg-laying hen, the improvement which comprises:
    combining neat poultry semen with a conventional poultry semen diluent in a ratio sufficiently large to ensure an adequate number of spermatozoa per volume of mixture for fertilization and sufficiently small to ensure easy and complete intermixing of semen and diluent, said diluent containing an amount of a poultry fertility-enhancing prostaglandin (POFEN-PG) effective to prolong or intensify fertility in said hen when inseminated with the resulting semen-diluent mixture.

12. An improvement according to claim 11 wherein said ratio is not more than 5:1 or less than 1:5.

13. An improvement according to claim 11 wherein said ratio is 1:1.

14. An improvement according to claim 12 wherein said POFEN-PG is PGE$_1$, PGE$_2$, PGF$_1\alpha$, PGF$_2\alpha$, PGA$_1$, or PGA$_2$.

15. An improvement according to claim 12 wherein said POFEN-PG is PGA$_1$.

16. In a method for the artificial insemination of an egg-laying hen the improvement which comprises:
    concomitantly with the artificial insemination administering to said hen an amount of a poultry fertility-enhancing PG (POFEN-PG) effective to prolong or intensify fertility.

17. An improvement according to claim 16 wherein said administration is by intramuscular injection into said hen's breast.

18. An improvement according to claim 17 wherein said POFEN-PG is $PGE_1$, $PGE_2$, $PGF_1\alpha$, $PGF_2\alpha$, $PGA_1$, $PGA_2$.

19. An improvement according to claim 18 wherein said POFEN-PG is $PGA_1$.

* * * * *

UNITED STATES PATENT OFFICE
CERTIFICATE OF CORRECTION

Patent No. 4,094,972          Dated June 13, 1978

Inventor(s)    Bernard James Marquez

It is certified that error appears in the above-identified patent and that said Letters Patent are hereby corrected as shown below:

Column 5, line 47, "semi-diluent" should read -- semen-diluent --;

Column 6, line 19, "PGE, $PGE_2$," should read -- $PGE_1$, $PGE_2$, --.

Signed and Sealed this

Fourteenth Day of November 1978

[SEAL]

Attest:

RUTH C. MASON
*Attesting Officer*

DONALD W. BANNER
*Commissioner of Patents and Trademarks*